United States Patent
Inoue

(10) Patent No.: US 11,918,188 B2
(45) Date of Patent: Mar. 5, 2024

(54) ENDOSCOPE

(71) Applicant: FUJIFILM Corporation, Tokyo (JP)

(72) Inventor: Wataru Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 371 days.

(21) Appl. No.: 17/204,901

(22) Filed: Mar. 17, 2021

(65) Prior Publication Data

US 2021/0196103 A1  Jul. 1, 2021

Related U.S. Application Data

(63) Continuation of application No. PCT/JP2019/037481, filed on Sep. 25, 2019.

(30) Foreign Application Priority Data

Sep. 27, 2018 (JP) .................... 2018-182532

(51) Int. Cl.
  *A61B 1/00* (2006.01)
  *A61B 1/005* (2006.01)
  *A61B 1/05* (2006.01)

(52) U.S. Cl.
  CPC ............ *A61B 1/05* (2013.01); *A61B 1/00006* (2013.01); *A61B 1/00009* (2013.01); *A61B 1/00042* (2022.02); *A61B 1/0051* (2013.01)

(58) Field of Classification Search
  CPC ... A61B 1/05; A61B 1/00042; A61B 1/00006; A61B 1/00009; A61B 1/0051; A61B 1/00135; A61B 1/00142; A61B 1/00103; A61B 1/00128; A61B 1/00078; A61B 1/00071; A61B 118/1445; A61M 2039/267; A61M 2025/0681; A61F 2/962

USPC .......................................................... 600/118
See application file for complete search history.

(56) References Cited

U.S. PATENT DOCUMENTS

| | | | |
|---|---|---|---|
| 5,812,188 A | 9/1998 | Adair | |
| 2009/0176185 A1 | 7/2009 | Chen | |
| 2009/0247825 A1 | 10/2009 | Tanahashi | |
| 2016/0317006 A1* | 11/2016 | Gomez | ................ A61B 1/127 |
| 2018/0092520 A1 | 4/2018 | Michihata et al. | |
| 2018/0348502 A1 | 12/2018 | Tanahashi | |

FOREIGN PATENT DOCUMENTS

| | | |
|---|---|---|
| JP | H08544 | 1/1996 |
| JP | 2003210393 | 7/2003 |
| JP | 2006255107 | 9/2006 |

(Continued)

OTHER PUBLICATIONS

"Office Action of Japan Counterpart Application", dated Nov. 16, 2022, with English translation thereof, pp. 1-6.

(Continued)

*Primary Examiner* — Timothy J Neal
*Assistant Examiner* — James Edward Boice
(74) *Attorney, Agent, or Firm* — JCIPRNET

(57) ABSTRACT

There is provided an endoscope in which an operation switch included in the endoscope can be sealed with an airtight structure having a simple structure. A cable (16) of an endoscope (10) has a skin (52) that covers an outer periphery of the cable (16), the skin (52) defines an airtight space (17) inside the cable (16), and an operation switch (50) is disposed in the airtight space (17).

11 Claims, 10 Drawing Sheets

(56) References Cited

FOREIGN PATENT DOCUMENTS

| | | | | |
|---|---|---|---|---|
| JP | 2006255107 | A | * | 9/2006 |
| JP | 2007196017 | | | 8/2007 |
| JP | 2009233173 | | | 10/2009 |
| JP | 2010099181 | | | 5/2010 |
| JP | 2010099181 | A | * | 5/2010 |
| JP | 2018057509 | | | 4/2018 |
| JP | 2018075461 | | | 5/2018 |

OTHER PUBLICATIONS

"International Search Report (Form PCT/ISA/210) of PCT/JP2019/037481," dated Dec. 17, 2019, with English translation thereof, pp. 1-5.
"Written Opinion of the International Searching Authority (Form PCT/ISA/237) of PCT/ JP2019/037481," dated Dec. 17, 2019, with English translation thereof, pp. 1-10.
"Search Report of Europe Counterpart Application", dated Sep. 23, 2021, p. 1-p. 7.
"Office Action of Japan Counterpart Application", dated Jun. 13, 2022, with English translation thereof, p. 1-p. 6.

* cited by examiner

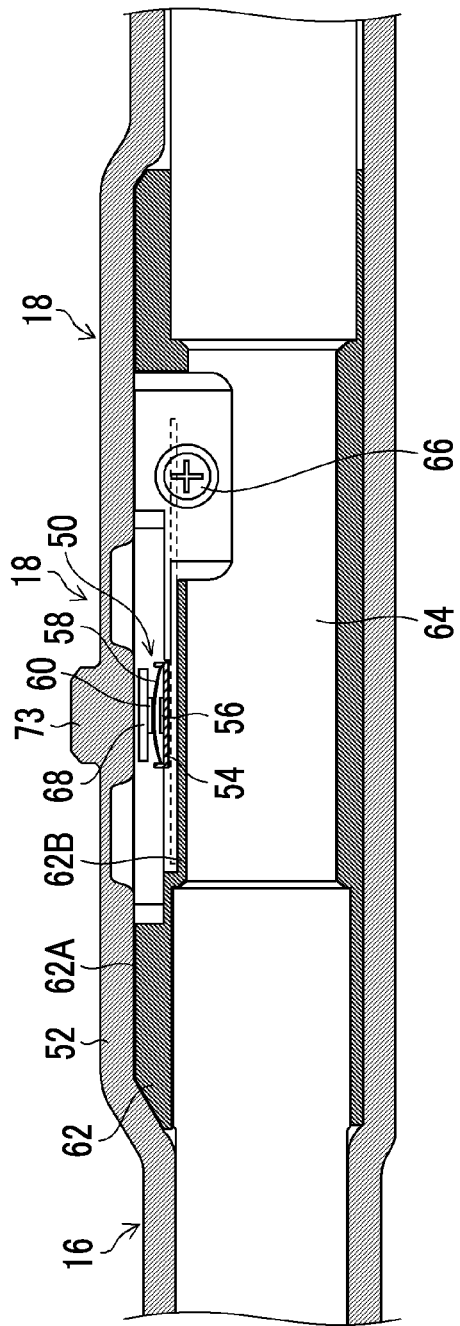

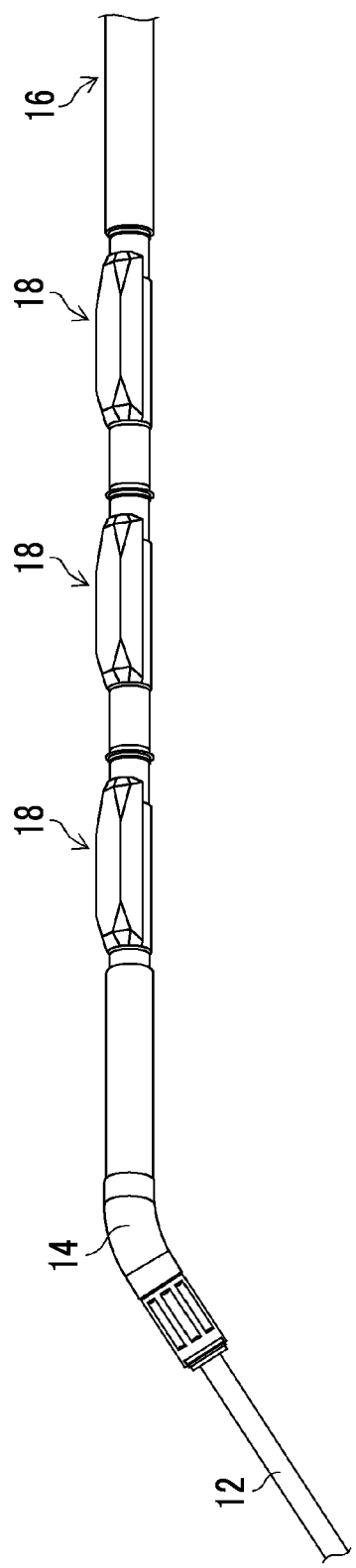

ENDOSCOPE

CROSS-REFERENCE TO RELATED APPLICATIONS

The present application is a Continuation of PCT International Application No. PCT/JP2019/037481 filed on Sep. 25, 2019 claiming priority under 35 U.S.C § 119(a) to Japanese Patent Application No. 2018-182532 filed on Sep. 27, 2018. Each of the above applications is hereby expressly incorporated by reference, in its entirety, into the present application.

BACKGROUND OF THE INVENTION

1. Field of the Invention

The present invention relates to an endoscope, and relates particularly to an endoscope comprising an operation switch for performing various settings in endoscopic surgery.

2. Description of the Related Art

In recent years, since invasion to a patient is small compared to surgery in which a laparotomy, a thoracotomy, or the like is performed, endoscopic surgery using endoscopes (rigid endoscopes), such as a laparoscope, is widely performed. A rigid endoscope is configured to comprise an elongated rigid insertion part which is inserted into a body cavity, a grip part which is connected to a proximal end portion of the insertion part, and a flexible cable, of which a proximal end portion is connected to the insertion part via the grip part.

JP2007-196017A discloses such a rigid endoscope in which a switch arranged part is provided in a grip part. The switch arranged part comprises a plurality of remote switches for remotely controlling a video recording device, such as a video tape recorder, a camera control unit, or the like.

In addition, JP2009-233173A discloses a rigid endoscope in which a remote control unit is provided in the middle of a camera cable. A plurality of push switches are provided in this remote control unit.

However, an endoscope (for example, a colonoscope, a gastroscope, or the like) is washed and disinfected after being used. In particular, an autoclave device for the rigid endoscope is a device that performs sterilization processing on the endoscope using high-temperature and high-pressure air, and performs sterilization processing by exposing the endoscope, for example, under an environment where saturated water vapor is at 2 atm and at 121° C., for approximately 20 minutes. The temperature, atmospheric pressure, and time set in the autoclave device are examples.

Since the endoscope is exposed to a high-pressure environment at the time of sterilization processing by the autoclave device, the endoscope comprises an airtight structure that seals a gap between components configuring the endoscope such that water vapor does not infiltrate into devices of the endoscope from the gap. In addition, even the rigid endoscope comprising an operation switch requires an airtight structure that seals a gap around the operation switch.

JP2018-075461A discloses an endoscope comprising a switch unit having an airtight structure. The switch unit comprises a frame body, which is fixed to an opening portion and in which a plurality of holes are formed, a plurality of switches which are provided in two holes respectively among the plurality of holes, a flexible switch cover which covers the plurality of switches, a first locking part which is formed on the switch cover at a position between the plurality of switches, a switch fixing member, which fixes the plurality of switches, that are arranged in the two holes respectively and are covered with the switch cover, to the opening portion, and to which the first locking part is locked at a position facing the first locking part, and a second locking part which is formed on an outer periphery of the switch cover and is locked to the frame body.

SUMMARY OF THE INVENTION

However, in a case where an airtight structure having a complicated structure as disclosed in JP2018-075461A is applied as the airtight structure for the operation switch included in the rigid endoscope, there are a problem in which the structure of the operation switch becomes complicated attributable to the airtight structure and a problem in which the weight of the rigid endoscope increases.

The present invention is devised in view of such circumstances, and an object thereof is to provide an endoscope in which an operation switch included in the endoscope can be sealed with an airtight structure having a simple structure.

According to an aspect of the present invention, in order to achieve the object of the present invention, there is provided an endoscope comprising a rigid insertion part that is inserted into a body, a flexible cable that is connected to a proximal end side of the insertion part, and an operation switch that is disposed in the cable. The cable has a skin covering an outer periphery of the cable, and the skin defines an airtight space inside the cable. The operation switch is disposed in the airtight space.

According to the aspect of the present invention, it is preferable that the operation switch comprises a push member at a position facing a surface of the skin on an airtight space side.

According to the aspect of the present invention, it is preferable that a base member to which the operation switch is attached is provided in the airtight space.

According to the aspect of the present invention, it is preferable that the base member has an insertion port at each of a distal end portion on an insertion part side and a proximal end portion on an opposite side to the insertion part side.

According to the aspect of the present invention, it is preferable that the base member has a recessed portion accommodating the operation switch.

According to the aspect of the present invention, it is preferable that a plate-shaped body having a surface area larger than the push member is disposed between the push member and the surface of the skin on the airtight space side.

According to the aspect of the present invention, it is preferable that a tubular cover rubber mounted on an outer peripheral portion of the cable is further included, an elastically deformable button portion is formed on an outer surface of the cover rubber in a protruding manner, and the cover rubber is mounted on the cable in a state where the button portion faces the operation switch.

According to the aspect of the present invention, it is preferable that an elastically deformable button portion is formed on the skin in a protruding manner, and the operation switch is disposed in the airtight space in a state of facing the button portion.

According to the aspect of the present invention, it is preferable that a plurality of the operation switches are disposed in the cable.

According to the aspect of the present invention, it is preferable that the operation switch is an image switching switch, an image immobilizing switch, an imaging switch, a zoom switch, a washing switch, a light amount adjusting switch, or a sensitivity adjusting switch.

According to the aspect of the present invention, it is preferable that the operation switch is a tactile switch.

According to the aspect of the present invention, it is preferable that the operation switch is a membrane switch.

With the present invention, the operation switch included in the endoscope can be sealed with the airtight structure having a simple structure.

BRIEF DESCRIPTION OF THE DRAWINGS

FIG. 9 is a cross-sectional view of the switch disposed part in which a button portion is formed in a protruding manner on a skin positioned at the switch disposed part.

FIG. 10 is an enlarged perspective view in which a plurality of switch disposed parts are disposed in the middle portion of the cable.

DESCRIPTION OF THE PREFERRED EMBODIMENTS

Hereinafter, an endoscope according to an embodiment of the present invention will be described with reference to the accompanying drawings.

Figure 1:
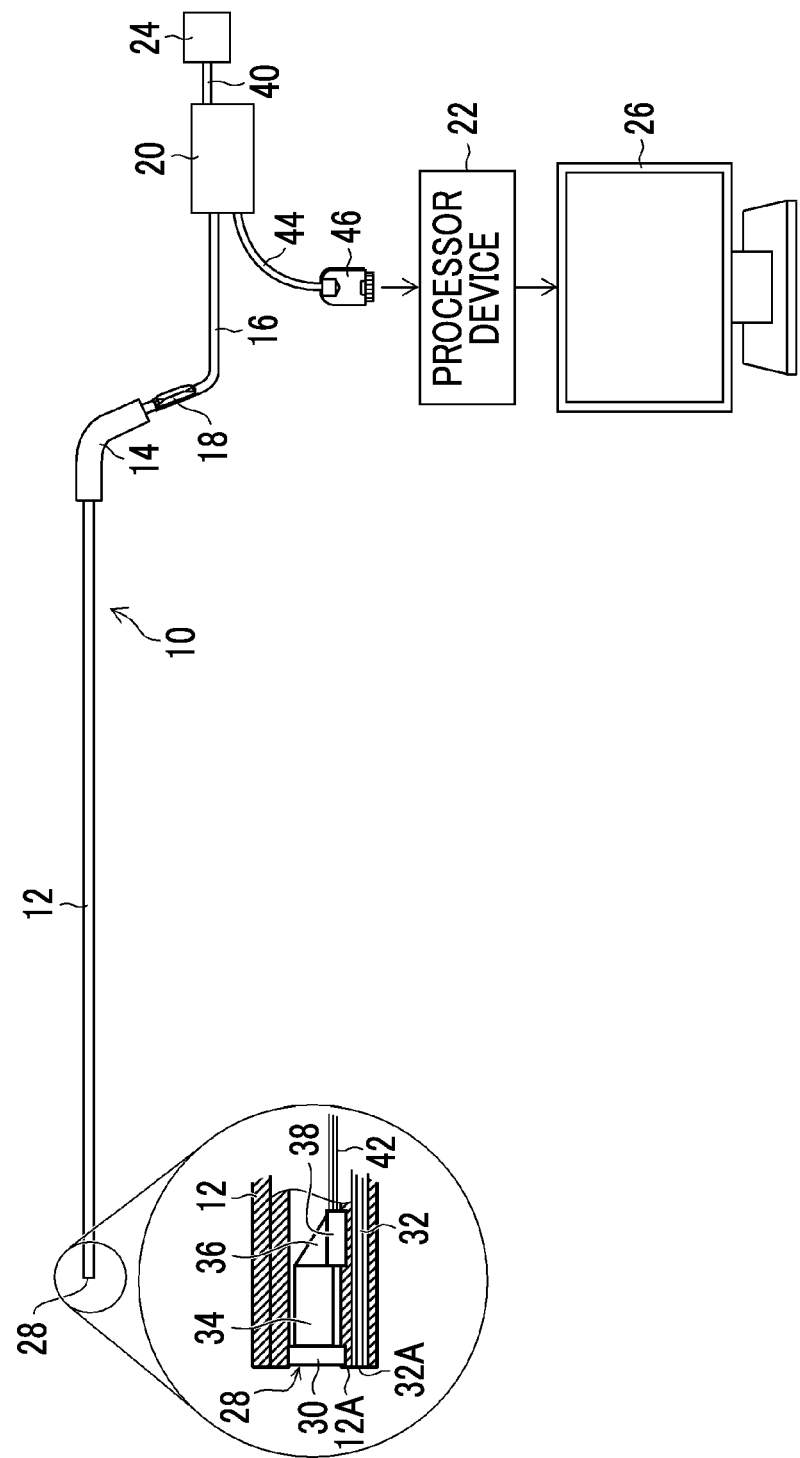
FIG. 1 is a schematic configuration view of a rigid endoscope of an embodiment.

FIG. 1 is an overall view of an endoscope 10 according to the embodiment.

The endoscope 10 illustrated in FIG. 1 is a rigid endoscope such as a laparoscope, and is inserted into a body cavity to observe the inside of the body cavity. The endoscope 10 comprises an elongated rigid insertion part 12 that is inserted into the body cavity, an L-shaped grip part 14 connected to a proximal end portion of the insertion part 12, a flexible cable 16 connected to a proximal end side of the insertion part 12 via the grip part 14, and a switch disposed part 18 provided in a middle portion of the cable 16.

A connector device 20 is provided at a proximal end portion of the cable 16, and a processor device 22 and a light source device 24 are attachably and detachably connected to the endoscope 10 via the connector device 20. In addition, a monitor 26 is connected to the processor device 22.

Figure 2:
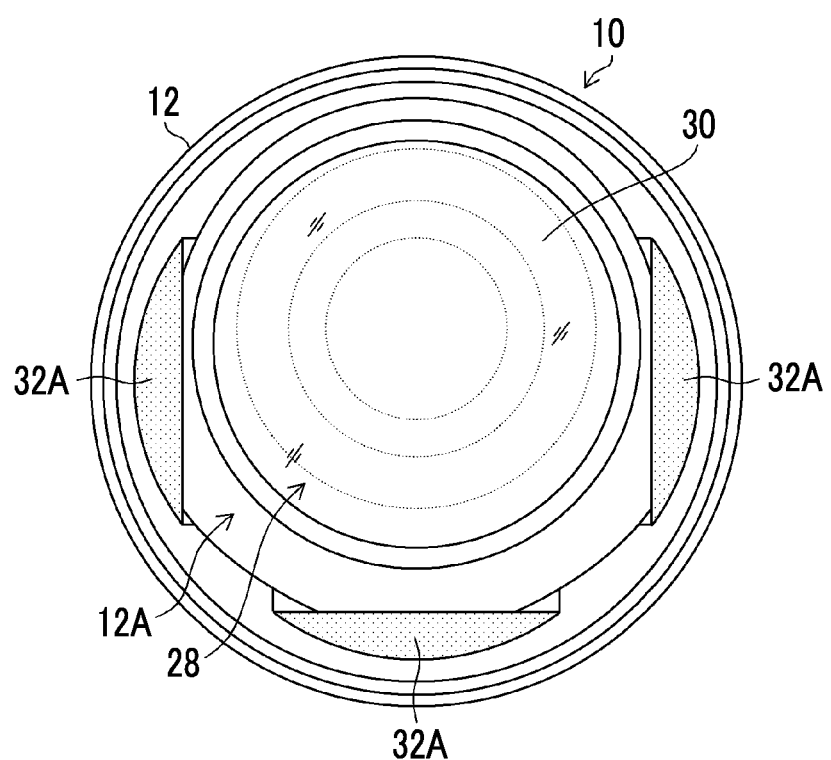
FIG. 2 is a front view of a distal end portion of an insertion part of the rigid endoscope.

FIG. 2 is a front view of a distal end portion of the insertion part 12. FIG. 1 illustrates an enlarged cross section of main parts at the distal end portion of the insertion part 12.

As illustrated in FIGS. 1 and 2, an observation part 28 is provided on a distal end surface 12A of the insertion part 12. The observation part 28 comprises an observation window 30, an emission end 32A that is a distal end portion of a light guide 32, which is disposed around the observation window 30, an image pickup lens group 34 and a prism 36 that are disposed at a rear part of the observation window 30, and a solid-state imaging element 38. As the solid-state imaging element 38, a charge coupled device (CCD) image sensor or a complementary metal oxide semiconductor (CMOS) image sensor can be used.

A proximal end portion of the light guide 32 is connected to a light guide rod 40 of the connector device 20 by being inserted into the insertion part 12, the grip part 14, and the cable 16, and is connected to the light source device 24 via the light guide rod 40. Accordingly, illumination light radiated from the light source device 24 is transmitted via the light guide 32, and is radiated to the front of the insertion part 12 from three emission ends 32A of the light guide 32. Consequently, the inside of the body cavity of a patient is illuminated.

On the other hand, subject light picked up from the observation window 30 is formed as an image on an imaging surface of the solid-state imaging element 38 via the image pickup lens group 34 and the prism 36, and is converted to an image pickup signal by the solid-state imaging element 38. A distal end portion of a signal line 42 is connected to the solid-state imaging element 38 via a base substrate (not illustrated). A proximal end portion of the signal line 42 is connected to the connector device 20 by being inserted into the insertion part 12, the grip part 14, and the cable 16. Then, the signal line 42 is accommodated in a video cable 44 of the connector device 20, and is connected to a connector 46 linked to a distal end portion of the video cable 44. By the connector 46 being connected to the processor device 22, the processor device 22 causes the monitor 26 to display an endoscopic image based on the image pickup signal input by the solid-state imaging element 38.

Next, the switch disposed part 18 included in the endoscope 10 of the embodiment will be described.

Figure 3:
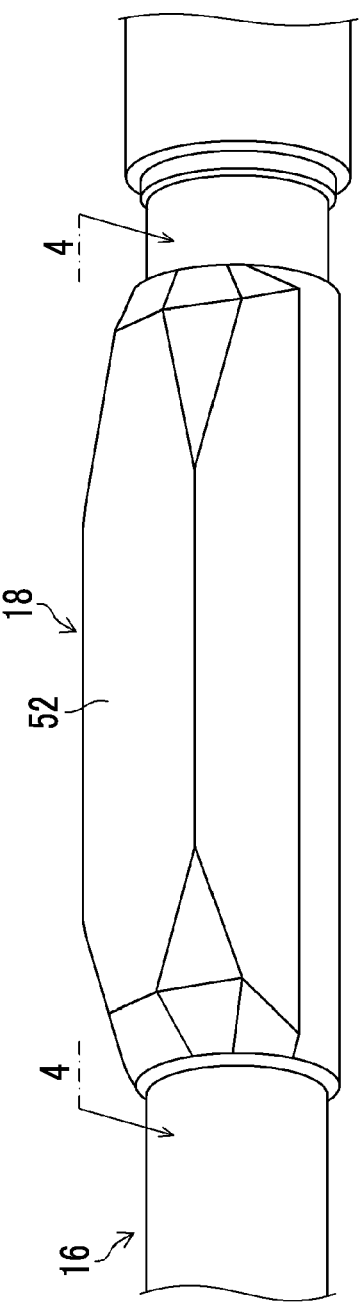
FIG. 3 is an enlarged perspective view of a switch disposed part disposed in a middle portion of a cable.
Figure 4:
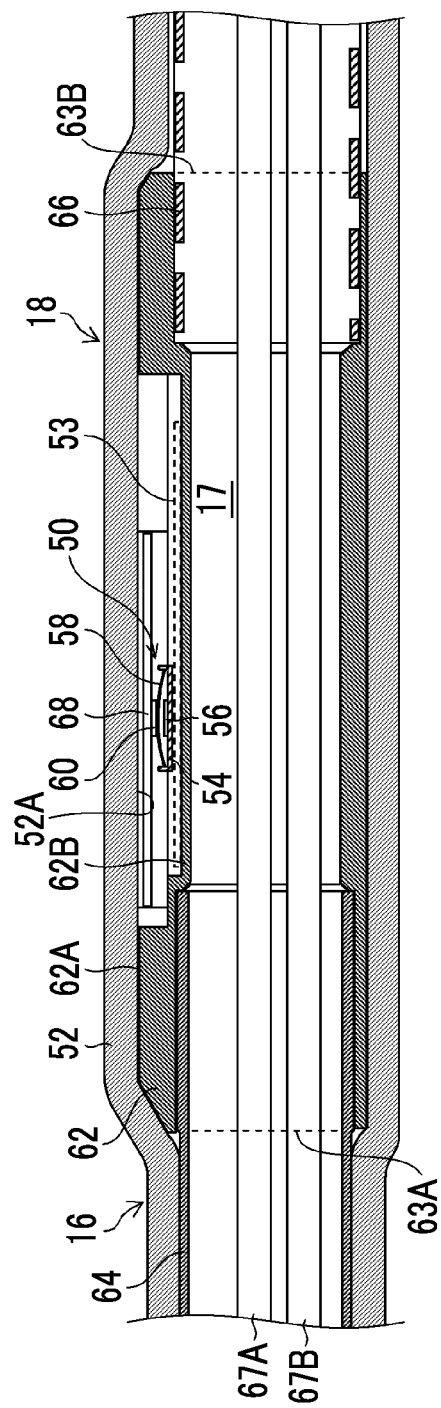
FIG. 4 is a cross-sectional view taken along line 4-4 of FIG. 3.
Figure 5:
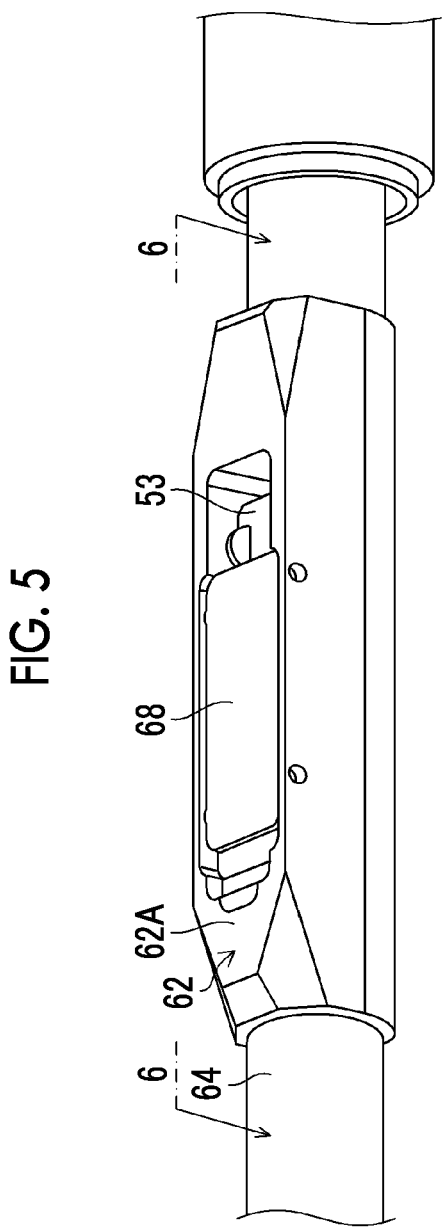
FIG. 5 is a perspective view illustrating a configuration of an operation switch.
Figure 6:
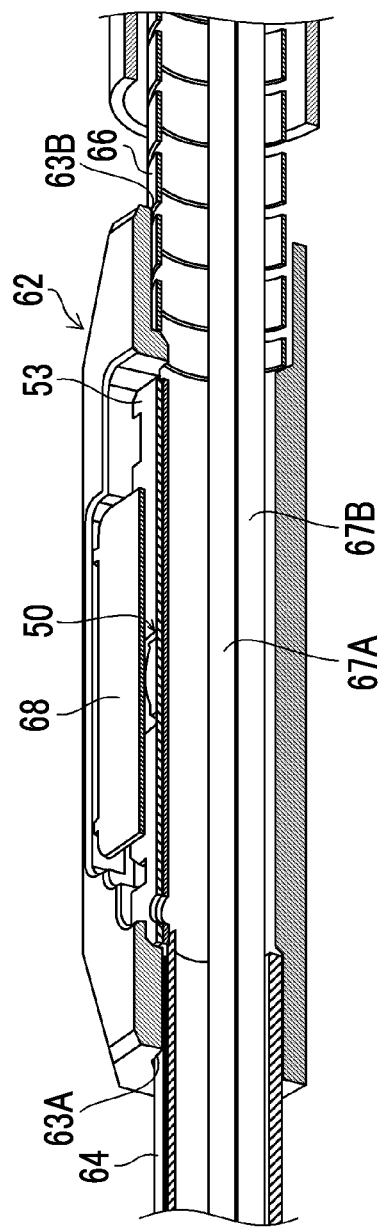
FIG. 6 is a cross-sectional view taken along line 6-6 of FIG. 5.

FIG. 3 is an enlarged perspective view of the switch disposed part 18 disposed in the middle portion of the cable 16. FIG. 4 is a cross-sectional view of the switch disposed part 18 taken along line 4-4 of FIG. 3. FIG. 5 is a perspective view of an operation switch 50 disposed at the switch disposed part 18, and illustrates an external shape of the operation switch 50 in a case where a skin 52 covering an outer periphery of the cable 16 is removed. FIG. 6 is a cross-sectional view taken along line 6-6 of FIG. 5.

The switch disposed part 18 of the embodiment is configured by disposing the operation switch 50 and wiring (not illustrated) connected to the operation switch 50 in an airtight space 17 inside the cable 16, which is defined by the skin 52, as illustrated in FIG. 4. In addition, the operation switch 50 is configured to be operable through pressing via the skin 52 from the outside of the cable 16. Although a configuration of the operation switch 50 will be described later, as the operation switch 50 is disposed in the airtight space 17 inside the cable 16, which is defined by the skin 52, to ensure airtightness, the endoscope 10 of the embodiment has resistance at the time of sterilization processing by an autoclave device.

The airtightness of the airtight space 17 inside the cable 16 is usually defined through the following configuration. That is, the skin 52 is configured as one tubular member having no boundary in the middle. A gap between a distal end portion of the skin 52 and a proximal end portion of the grip part 14 is filled and sealed with an adhesive. In addition, a gap between the proximal end portion of the cable 16 and a distal end portion of the connector device 20 is filled and sealed with an adhesive. Airtightness is defined by such a configuration of the skin 52 and an adhesive filling structure.

Since the endoscope 10 of embodiment has adopted a configuration where the operation switch 50 is disposed in the airtight space 17 inside the cable 16, of which airtightness is defined by the skin 52, it is not necessary to add an airtight structure, which is dedicated to the operation switch 50, to the operation switch 50, and accordingly, the operation switch 50 can be sealed with an airtight structure having a simple structure. Accordingly, since the structure of the operation switch 50 is simplified and the weight of the endoscope 10 is reduced, the operability of the endoscope 10 improves.

Hereinafter, a case where a tactile switch having a known configuration is applied as the operation switch 50 of the embodiment will be described.

As illustrated in FIG. 4, the tactile switch is a switch that comprises a base 54 connected to a foundation 53, a fixed contact 56 fixed to the base 54, a dome-shaped movable contact 58, and a push member 60, and operates an operated part as the push member 60 is pressed to bring the movable contact 58 into contact with the fixed contact 56. As illustrated in FIGS. 4 to 6, the base 54 of the tactile switch is attached to a base member 62 via the foundation 53.

The base member 62 is provided in the airtight space 17. In addition, the base member 62 is configured in a tubular shape, has an insertion port 63A at a distal end portion on an insertion part 12 (refer to FIG. 1) side, and has an insertion port 63B at a proximal end portion on an opposite side to the insertion part 12 side. A proximal end portion of a tube 64 arranged in the airtight space 17 is inserted and fixed to the insertion port 63A of the base member 62, and a distal end portion of a spiral tube 66 arranged in the airtight space 17 is inserted and fixed to the insertion port 63B of the base member 62. By using such a base member 62, the tactile switch can be stably disposed in the airtight space 17. An embodiment of fixing the tube 64 to the insertion port 63A and an embodiment of fixing the spiral tube 66 to the insertion port 63B are not particularly limited, and for example, a fastening member such as a screw and a bolt, can be exemplified. In addition, a tactile switch (model number: SKSWCFE010 or SKSWCFE010) manufactured by Alps Alpine or a tactile switch (model number: EVPAWCD4A or EVPAWBD4A) manufactured by Panasonic can be exemplified as a tactile switch to be mounted.

As illustrated in FIG. 6, two tubes 67A and 67B each of which has a small diameter are inserted and disposed inside the tube 64, the base member 62, and the spiral tube 66, the light guide 32 (refer to FIG. 1) is inserted in the tube 67A, and the signal line 42 (refer to FIG. 1) is inserted in the tube 67B. Although the base member 62 is configured in a tubular shape in the embodiment, without being limited thereto, the base member may be in a shape of having at least the insertion ports 63A and 63B. Specifically, an embodiment in which a distal end ring part comprising the insertion port 63A and a proximal end ring part comprising the insertion port 63B are connected by a plate-shaped connecting member may be adopted.

For example, a heat-stretchable silicone tube can be applied as the skin 52. By inserting the base member 62 into the skin 52 and thermally contracting the skin 52, the convex switch disposed part 18 to which the shape of the base member 62 is transferred is configured in the middle portion of the cable 16 as in FIG. 3. Although a position where the push member 60 is disposed in a circumferential direction of the skin 52 is not particularly limited, in a case where a surgeon holds the grip part 14 and directs the insertion part 12 toward the front of the surgeon, the insertion part is disposed at a position facing the surgeon in the embodiment.

Next, a structure of attaching the tactile switch to the base member 62 will be described.

First, in a case where the push member 60 of the tactile switch is attached with the push member protruding from an outer surface 62A of the base member 62, the push member 60 is pressed by the skin 52 in some cases where the skin 52 has thermally contracted. Therefore, in the endoscope 10 of embodiment, a recessed portion 62B is formed in the base member 62, the tactile switch is accommodated in the recessed portion 62B, and the push member 60 is disposed so as not to protrude from the outer surface of the base member 62. Accordingly, the push member 60 can be effectively operated.

In addition, since an extremely small switch is applied as the tactile switch disposed in the airtight space 17, the size of each of components configuring the tactile switch is also small. Against this background, in a case where a member having a small size (for example, a disk having a diameter of 1 mm) is applied as the push member 60, it is difficult for the push member 60 to be pressed (via the skin 52). Therefore, in such a case, it is preferable to dispose, between the push member 60 and a surface 52A (refer to FIG. 4) of the skin 52 on an airtight space 17 side, a rectangular plate 68 having a surface area (for example, a short side is 3 mm and a long side is 7 mm) larger than the push member 60. Accordingly, since the push member 60 can be indirectly pressed via the plate 68, it is easy to press the push member 60. In addition, in a case where the plate 68 is disposed, it is preferable to make a gap between the plate 68 and the surface 52A as small as possible. Accordingly, since a deformation amount of the surface 52A that deforms in a case of pressing the skin 52 can be made small, burden on the surface 52A can be alleviated. Although a plate-shaped body made of a metal having high stiffness is preferable as the plate 68, a plate-shaped body made of a resin may be used insofar as stiffness can be ensured. In addition, the shape of the plate 68 may be circular, or may be another shape.

Figure 7:
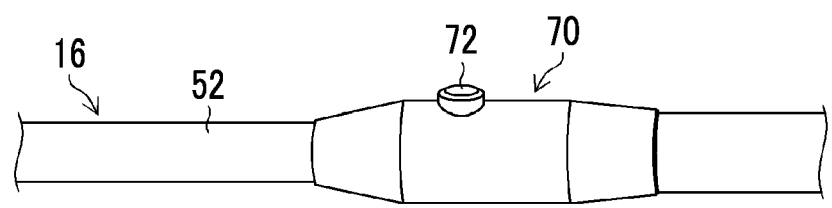
FIG. 7 is an explanatory view in which a cover rubber is mounted on the switch disposed part illustrated in FIG. 3.
Figure 8:
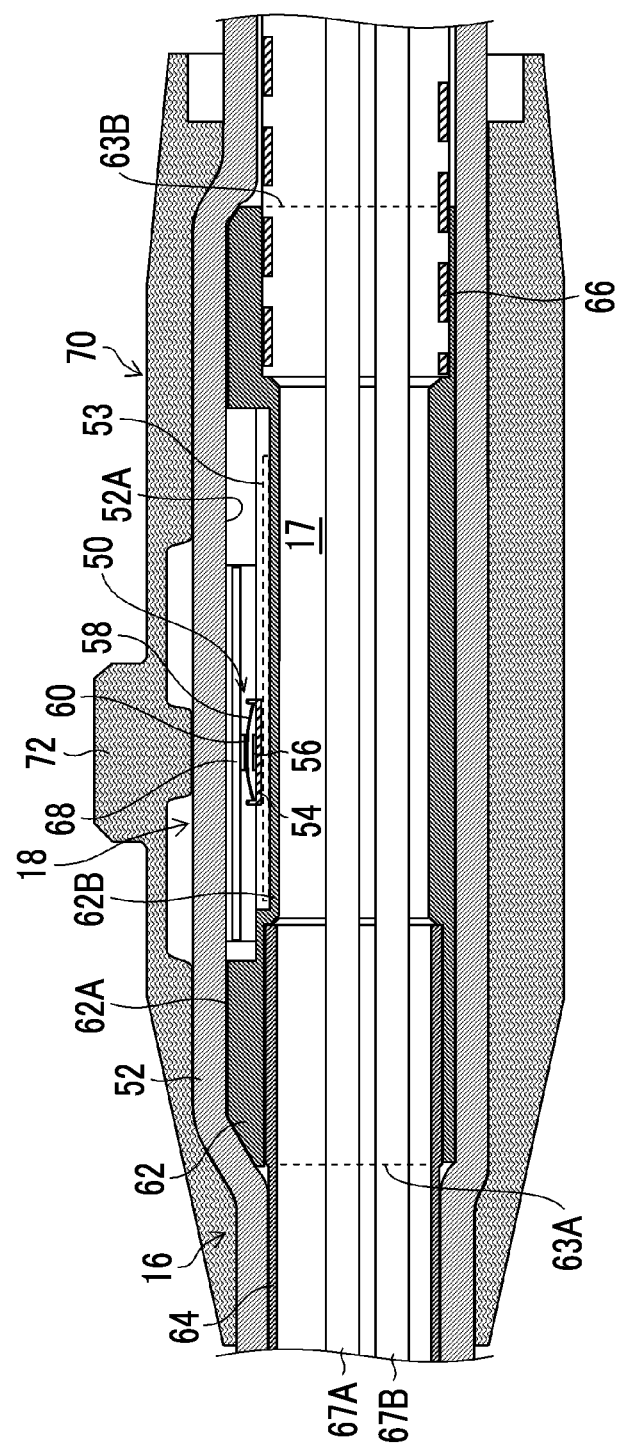
FIG. 8 is a cross-sectional view of the switch disposed part including the cover rubber of FIG. 7.

FIG. 7 is an explanatory view in which a cover rubber 70 is mounted on an outer peripheral portion of the cable 16 illustrated in FIG. 3. FIG. 8 is a cross-sectional view of the switch disposed part 18 including the cover rubber 70.

The cover rubber 70 illustrated in FIGS. 7 and 8 is configured in a tubular shape and is elastically mounted on the outer peripheral portion of the cable 16, in which the switch disposed part 18 is positioned. On an outer surface of the cover rubber 70, an elastically deformable button portion 72 is formed in a protruding manner. As illustrated in FIG. 8, the cover rubber 70 is mounted on the cable 16 in a state where the button portion 72 faces the operation switch 50. As such a cover rubber 70 is included, the following effects can be obtained.

That is, although it is necessary to learn the position of the operation switch 50 with a sensation caused when touching with a finger or the like in a state where the operation switch 50 is disposed in the airtight space 17, as the cover rubber 70 is mounted on the cable 16 and the button portion 72 is caused to face the operation switch 50, a surgeon can instantly and easily learn the position of the operation switch 50 with the button portion 72 as an indicator.

In addition, although the cover rubber 70 comprising the button portion 72 is mounted on the outer peripheral portion of the cable 16 in the example, a structure, in which an elastically deformable button portion 73 is formed in a protruding manner on the skin 52 positioned at the switch disposed part 18, and the operation switch 50 faces the button portion 73, may be adopted as illustrated in a cross-sectional view of the switch disposed part 18 of FIG. 9. Accordingly, it is possible to instantly and easily learn the position of the operation switch 50 without using the cover rubber 70.

As the operation switch 50 of the embodiment, an image switching switch that switches, as an image to be displayed on the monitor 26, between a normal captured image and a special light image (for example, a white light (WL) image, a blue laser imaging (BLI) image, a linked color imaging (LCI) image, or a hypoxia imaging image) can be exemplified. In addition, without being limited to the image switching switch, an image immobilizing switch, an imaging switch, a zoom switch comprising a telephoto and wide-angle buttons, a scope distal end washing switch, a light amount adjusting switch comprising large and small buttons, a sensitivity adjusting switch comprising high and low buttons, or the like can be exemplified.

In addition, as illustrated in FIG. 10, a plurality of (three in FIG. 10) switch disposed parts 18 may be disposed on the cable 16. In this case, it is preferable to assign the switch to the operation switch 50 (refer to FIG. 4) of each of the switch disposed parts 18. For example, in an embodiment in which three switch disposed parts 18 are provided as in FIG. 10, an image switching switch can be assigned as one of the operation switches 50, and light intensity switches can be assigned as two of the operation switches 50 and 50. In addition, although the plurality of switch disposed parts 18 illustrated in FIG. 10 are disposed along a longitudinal direction of the cable 16, the switch disposed parts may be disposed along a circumferential direction of the cable 16.

In addition, the operation switch 50 is not limited to the tactile switch, and for example, a membrane switch comprising a push member may be adopted. Since the tactile switch and the membrane switch realize a clicking sensation with a switch alone, a switch operating sensation can be given to a surgeon even in a case where the operation switch 50 is invisible.

In addition, as for a position where the operation switch 50 is disposed with respect to the cable 16, for example, it is preferable that the operation switch is disposed at a position within a range where operation is possible in a state where the grip part 14 is held such that a surgeon holding the grip part 14 easily operates. Specifically, in a case where the grip part 14 is held by the thumb, the index finger, and the middle finger of the hand, it is preferable to dispose the operation switch 50 at a position within a range where the operation switch can be operated by the middle finger or the little finger.

In addition, it is suitable to use the endoscope 10 of the embodiment in combination with an endoscopic surgical device (for example, refer to JP2017-080437A) which is used by being inserted into one mantle tube together with an endoscopic treatment tool such as high-frequency forceps. In this case, it is preferable to dispose the operation switch 50 at a position separated to a connector device 20 side from the disposed position so as not to interfere with a treatment tool operation part provided at a proximal end portion of the endoscopic treatment tool. Accordingly, since the operation switch 50 does not get in the way when operating the treatment tool operation part, and the treatment tool operation part does not get in the way when operating the operation switch 50, the usability of the endoscopic surgical device improves.

Although the embodiment of the present invention has been described hereinbefore, the present invention is not limited to the examples, and it is evident that various improvements and modifications may be made without departing from the gist of the present invention.

EXPLANATION OF REFERENCES

10: endoscope
12: insertion part
12A: distal end surface
14: grip part
16: cable
17: airtight space
18: switch disposed part
20: connector device
22: processor device
24: light source device
26: monitor
28: observation part
30: observation window
32: light guide
32A: emission end
34: image pickup lens group
36: prism
38: solid-state imaging element
40: light guide rod
42: signal line
44: video cable
46: connector
50: operation switch
52: skin
52A: surface
53: foundation
54: base
56: fixed contact
58: movable contact
60: push member
62: base member
62A: outer surface
62B: recessed portion
63A: insertion port
63B: insertion port
64: tube
66: spiral tube
67A: tube
67B: tube
68: plate
70: cover rubber
72: button portion
73: button portion

What is claimed is:

1. An endoscope comprising:
a rigid insertion part that is inserted into a body;
a flexible cable that is connected to a proximal end side of the insertion part;
an operation switch that is disposed in the cable; and
a tubular cover rubber mounted on an outer peripheral portion of the cable,
wherein the cable has a skin covering an outer periphery of the cable, and the skin defines an airtight space inside the cable, and
the operation switch is disposed in the airtight space,
wherein an elastically deformable button portion is formed on an outer surface of the cover rubber in a protruding manner, and
the cover rubber is mounted on the cable in a state where the button portion faces the operation switch, wherein the skin is between the button portion and the operation switch.

2. The endoscope according to claim 1,
wherein the operation switch comprises a push member at a position facing a surface of the skin on an airtight space side.

3. The endoscope according to claim 2,
wherein a base member to which the operation switch is attached is provided in the airtight space.

4. The endoscope according to claim 3,
wherein the base member has an insertion port at each of a distal end portion on an insertion part side and a proximal end portion on an opposite side to the insertion part side.

5. The endoscope according to claim 4,
wherein the base member has a recessed portion accommodating the operation switch.

6. The endoscope according to claim 5,
wherein a plate-shaped body having a surface area larger than the push member is disposed between the push member and the surface of the skin on the airtight space side.

7. The endoscope according to claim 1,
wherein the elastically deformable button portion is formed on the skin in a protruding manner, and
the operation switch is disposed in the airtight space in a state of facing the button portion.

8. The endoscope according to claim 1,
wherein a plurality of the operation switches are disposed in the cable.

9. The endoscope according to claim 1,
wherein the operation switch is an image switching switch, an image immobilizing switch, an imaging switch, a zoom switch, a washing switch, a light amount adjusting switch, or a sensitivity adjusting switch.

10. The endoscope according to claim 1,
wherein the operation switch is a tactile switch.

11. The endoscope according to claim 1,
wherein the operation switch is a membrane switch.

* * * * *